United States Patent [19]

Inoue et al.

[11] Patent Number: 5,175,084

[45] Date of Patent: Dec. 29, 1992

[54] METHOD FOR THE DIAGNOSIS OF HEPATIC CARCINOMA

[75] Inventors: Kyoichi Inoue; Takafumi Ichida; Miki Miyagiwa, all of Toyama; Taro Hayakawa, Nagoya; Shuji Kodama; Kazushi Iwata, both of Takaoka, all of Japan

[73] Assignee: Fuji Yakuhin Kogyo Kabushiki Kaisha, Toyama, Japan

[21] Appl. No.: 382,789

[22] PCT Filed: Oct. 28, 1988

[86] PCT No.: PCT/JP88/01103

§ 371 Date: Jun. 23, 1989

§ 102(e) Date: Jun. 23, 1989

[87] PCT Pub. No.: WO89/03997

PCT Pub. Date: May 5, 1989

[30] Foreign Application Priority Data

Oct. 30, 1987 [JP] Japan .................. 62-273265

[51] Int. Cl.⁵ .................. G01N 33/53; G01N 33/574
[52] U.S. Cl. .................. 435/7.9; 435/7.92; 435/7.94; 435/7.23; 435/28; 436/518; 436/531; 436/534; 436/64; 530/391.1; 530/391.3
[58] Field of Search .......... 435/7.94, 7.9, 7.92, 435/7.23, 240.27; 436/811, 813, 548, 518, 524, 531; 530/387, 388.1, 391.1, 391.3

[56] References Cited

FOREIGN PATENT DOCUMENTS 0210665  9/1988  Japan .................. 435/7.94

2074727 11/1981 United Kingdom ..
02078   3/1989  World Int. Prop. O. ......... 435/7.94

OTHER PUBLICATIONS

Kodama et al (1989) Columbus, Ohio 110 (19):445 "EIA of Collagenase Inhibitor in Blood and Other Samples".
Stricklin et al. (1986) Clinical Research 34(2):783A "Immunolocalization of collagenase inhibitor in normal skin and the stroma of basal cell carcinoma".
Eisen et al., J. Lab. Clin. Med. 75, 258-263 (1970).
Cawston et al., Arthritis and Rheumatism, 27, No. 3, 285-290 (1984).
Fundamentals of Comparative Embryology of the Vertebrates by Alfred F. Huettner, New York, The MacMillan Company, 1949, p. 222.
Voller et al, "Enzyme-Linked Immunosorbent Assay" in Manual of Clinical Laboratory Immunology, pp. 99-109 (1986).

Primary Examiner—Esther L. Kepplinger
Assistant Examiner—Carol E. Bidwell
Attorney, Agent, or Firm—Birch, Stewart, Kolasch and Birch

[57] ABSTRACT

A method for diagnosing hepatic carcinoma, which is characterized by enzyme-immunologically measuring the amount of collagenase inhibitor present in sera, plasmas of synovial fluids by way of a sandwich assay wherein two different monoclonal antibodies which specifically bind to different antigenic determinants of the collagenase inhibitor are used, and comparing the measured amount with that for normal subjects.

20 Claims, 6 Drawing Sheets

Bovine dental pulp collagenase inhibitor (pg/tube)

METHOD FOR THE DIAGNOSIS OF HEPATIC CARCINOMA

FIELD OF THE INVENTION

The present invention relates to a method of the diagnosis for hepatic carcinoma by way of quantitation of collagenase inhibitor. More particularly the invention relates to a method for carrying out the diagnosis of hepatic carcinoma, by means of a sandwich enzyme immunoassay for human collagenase inhibitor using monoclonal antibodies to bovine collagenase inhibitor (tissue inhibitors of metalloproteinases: TIMP), on the basis of the fact that the amount of collagenase inhibitor in sera, plasmas or synovial fluids from patients with hepatic carcinoma is clearly higher than the amount of collagenase inhibitor in sera, plasmas or synovial fluids, respectively, from normal subjects. The enzyme immunoassay mentioned above is used to mean a method for determining collagenase inhibitor which is characterized in that there are used two different monoclonal antibodies which specifically bind to different antigenic determinants of collagenase inhibitor as an antibody to be bound to a solid phase support and an antibody to be labeled with an enzyme.

BACKGROUND ART

Collagenase inhibitor has been known to exist in human's and other animals' bones, skins, dental pulps, amniotic fluids, bloods and synovial fluids as well as in cultures of joint chondrocytes, synovial cells, fibroblasts derived from varied tissues and fibrosarcomatous cells. As means for determining the amount of collagenase inhibitor, methods have heretofore been known which are based on measurement of its biological activity. As described by Eisen et al. in J. Lab. Clin. Med. 75, 258–263 (1973) and also by Cawston et al. in Arthritis and Rheumatism 27, 285–290 (1984), however, it is impossible, with the heretofore known methods of determination, to assay sera, plasmas or synovial fluids for collagenase inhibitor activity since there exist in such fluids proteins, such as $\alpha_2$-macroglobulin, which interfere disturbingly with the measurement. Hayakawa, Iwata et al. have already developed a sandwich enzyme immunoassay (EIA) using monoclonal antibodies to bovine collagenase inhibitor, a method which enables specific quantitation of collagenase inhibitor with very small volumes of samples in a precise, straightforward and rapid manner (Japanese Patent Application No. Sho 62-42781). The present inventors have discovered that the level of collagenase inhibitor present in human sera, plasmas or synovial fluids apparently increases in association with affliction with hepatic carcinoma, and found that it is possible to make a diagnosis of hepatic carcinoma by determining, by the enzyme immunoassay mentioned above, the amount of collagenase inhibitor present in sera, plasmas or synovial fluids.

DISCLOSURE OF THE INVENTION

The present invention has been accomplished on the basis of the findings as mentioned above, and provides a method for diagnosing whether the subject is afflicted with hepatic carcinoma, which comprises carrying out an enzyme immunoassay by the sandwich method, with the aid of two different monoclonal antibodies that specifically bind to different antigenic determinants of bovine collagenase inhibitor as antibodies to be bound to a solid phase support and to be labeled with an enzyme, to measure the amount of human collagenase inhibitor present in the subject's sera, plasmas or synovial fluids, and comparing the measured amount with that for normal subjects.

The present inventors immunized Balb/c mice by intraperitoneal administration thereto of a solution containing collagenase inhibitor purified from culture media obtained by cultivating bovine dental pulps, and spleen cells were then removed from the mice. The spleen cells were mixed with 8-azaguanine-resistant myeloma cells NS-1 in a ratio of 5:1, and they were allowed to fuse together in 50% polyethyleneglycol 4000 to obtain hybridomas. The hybridomas were dispensed in a 96-well microwell made of polystyrene so that $6.0 \times 10^5$ cells exist in each well and then cultivated in HAT culture medium. The culture medium in each well was checked by a solid phase-antibody binding test (ELISA) for production of antibodies against bovine dental pulp collagenase inhibitor, and hybridomas in those wells that were positive in the test were cloned by means of the limiting dilution method. As a result, there were obtained seventeen monoclones capable of producing monoclonal antibody to bovine dental pulp collagenase inhibitor. Each of the monoclones was intraperitoneally administered to Balb/c mice to obtain ascites containing monoclonal antibody. From the ascites were purified monoclonal antibodies through salting-out fractionation with ammonium sulfate, ion exchange chromatography by DEAE-Sephacel, gel filtration on Sephacryl S-300 Superfine, etc. The thus purified seventeen monoclonal antibodies were all found to specifically cross-react with bovine collagenase inhibitor, and four out of them, i.e. IgG (clone 7-6C1), IgG (clone 7-19F6), IgG (clone 7-21B12) and IgG (clone 7-23G9), were revealed by Western blotting to react also with human collagenase inhibitor. A very small amount (1.5 pg) of human collagenase inhibitor could be quantitated in a specific and precise manner by carrying out a sandwich EIA with two out of four such monoclonal antibodies: IgG (clone 7-23G9) as the solid phase antibody, and IgG (clone 7-6C1) as the labeled antibody in the form of Fab' (clone 7-6C1)-POD prepared therefrom. The hybridomas FERM BP-3468 and FERM BP-3469, which produce monoclonal antibodies 7-6C1 and 7-23G9, respectively, have been deposited under the terms of the Budapest Treaty on Jul. 1, 1991 at the Fermentation Research Institute, Agency of Industrial Science and Technology, Tomoo Suzuki, Director General, 1-3, Higashi 1-chome, Tsukuba-shi, Ibaraki-ken, 305, Japan. This sandwich method was used to measure the amount of collagenase inhibitor in fifty samples of serum from normal subjects to find that $184\pm30$ ng of collagenase inhibitor was present in one ml of serum. On the other hand, the mean amounts of collagenase inhibitor present in one hundred samples of serum from patients with hepatocellular carcinoma and three such samples from those with metastatic liver carcinoma were $486\pm316$ ng and $1172\pm712$ ng per ml of serum, respectively, and these levels are apparently high as compared to those found in sera from normal subjects. In contrast, the mean amounts of collagenase inhibitor present in forty-six samples of serum from patients with liver cirrhosis, in forty-five such samples from those with chronic active hepatitis and in twenty-six such samples from those with chronic inactive hepatitis were $228\pm163$ ng, $233\pm88$ ng and $166\pm73$ ng per ml of serum, respectively, and therefore showed no significant difference as compared to those found in sera from normal subjects. It has thus been found, in the light of specifically high serum collagenase inhibitor levels for patients with hepatic carcinoma as compared to those for patients with other liver disorders, that it is possible, by quantitating collagenase inhibitor in a patient's serum, to diagnose whether the patient is afflicted with hepatic carcinoma. Moreover, whereas the amount of collagenase inhibitor present in twenty-six samples of plasma from normal subjects was $64\pm10$ ng per ml of plasma, that present in eight such samples from patients with hepatocellular carcinoma was $583\pm447$ ng per ml of plasma, thus being clearly high as compared to the plasma level for normal subjects.

The phenomenon of increased collagenase inhibitor level in serum or plasma is also observable not only with patients with hepatic carcinoma but also with those with rheumatoid arthritis. Consequently, by performing the measurement of serum collagenase inhibitor in combination with liver function tests such as ZTT (zinc sulfate turbidity test), GOT (glutamic oxaloacetic transaminase), GPT (glutamic-pyruvic transaminase), ALP (alkaline phosphatase), LDH (lactate dehydrogenase), $\gamma$-GTP ($\gamma$-glutamyl transpeptidase), PH (prolyl hydroxylase) and AFP ($\alpha$-fetoprotein), it is possible to diagnose whether the subject is afflicted with hepatic carcinoma.

In the above mentioned enzyme immunoassay employed according to the method of the present invention, a variety of materials in any usage forms which well adsorb passively antigens or antibodies may be chosen for use as solid supports, e.g. polystyrenes, polycarbonates, polypropylenes or polyvinyls in such forms as balls, microplates, sticks or test tubes. As the antibody to be labeled with an enzyme, there may be used an IgG fraction obtainable by the fractionation of a material containing antibodies with ammonium sulfate followed by purification on an anion exchange gel such as DEAE-Sephacel, as well as FAb' that specifically reacts with an antigen molecule and that is obtainable by its digestion with pepsin followed by reduction.

The method of the invention is, as mentioned above, for diagnosing whether the subject is afflicted with hepatic carcinoma by carrying out the quantitative determination of human collagenase inhibitor on the basis of an enzyme immunoassay with the aid of a combination of two monoclonal antibodies that specifically bind to different antigenic determinants of the collagenase inhibitor as antibodies to be bound to a solid phase support and to be labeled with an enzyme, followed by comparing the result with values for normal subjects.

The present invention will now be illustrated in more detail by way of the following examples, but it is to be noted that this invention is not limited thereto.

EXAMPLE 1

Preparation of monoclonal antibodies against bovine collagenase inhibitor (a) Preparation of antigen-bovine collagenase inhibitor:

In accordance with the procedure described by the present inventors in J. Biochem. 96, 395-404 (1984), collagenase inhibitor was purified from culture media obtained by cultivated in Eagle's MEM medium (supplied by Nissui Seiyaku) of root pulps from bovine unerupted wisdom teeth, using columns of Con A-Sepharose, Ultrogel AcA 44 and DE-52 cellulose. When examined by sodium dodecyl sulfatepolyacrylamide gel electrophoresis (SDS-PAGE) according to the method described by Laemmli et al. in J. Mol. Biol. 80, 579-599 (1973), the purified inhibitor showed a single band having a molecular weight of about 32,000 dalton (D).

(b) Preparation of antibody-producing cells:

Two 6-week-old female Balb/c mice were initially immunized intraperitoneally with 48 $\mu$g in 0.4 ml emulsion of purified bovine collagenase inhibitor described above in (a) in Freund's complete adjuvant. The mice then received, after 30 days, a booster injection of 84 $\mu$g of the bovine collagenase inhibitor dissolved in saline. As the final immunization, the mice received, after 58 days, an additional booster injection by intraperitoneal administration of 95 $\mu$l/500 $\mu$l of the inhibitor in saline. On the 3rd day after the final immunization the spleen was extirpated and the spleen cells were prepared.

(c) Cell fusion:

(1) Materials and methods used are as follows:

RPMI 1640 culture medium: RPMI No. 1640 (Difco Laboratories) supplemented with sodium bicarbonate (12 mM), sodium pyruvate (1 mM), L-glutamine (2 mM), penicillin G potassium (50 U/ml), streptomycin sulfate (50 $\mu$g/ml) and amikacin sulfate (100 $\mu$g/ml), adjusted to pH 7.2 with dry ice and filtered through a 0.2 $\mu$m Toyo membrane filter for sterilization.

NS-1 culture medium: the above RPMI 1640 culture medium supplemented with 15% (v/v) fetal bovine serum (M.A. Bioproducts) filter-sterilized.

PEG 4,000 solution: Serum-free RPMI 1640 culture medium, containing 50% (w/w) polyethylene glycol 4,000 (PEG 4,000, Merck & Co., Inc.).

Utilizing an 8-azaguanine-resistant myeloma cell line, NS-1 (P3-NS1-1), cell fusion was effected according to a slightly modified method of Oi et al. described in "Selected Methods in Cellular Immunology" (ed. B. B. Mishell and S. M. Shiigi, W. H. Freeman and Company, (1980), pp. 351-372).

(2) The karyo-splenocytes prepared as described in the preceding (b) (cell viability 100%) were fused in a ratio of 5 to 1 with myeloma cells (cell viability 100%). Thus, the splenocytes and the myeloma cells were separately washed in RPMI 1640 culture medium, then suspended in the same medium and mixed together for fusion in the ratio described above. 40 ml of the RPMI 1640 culture medium was put into a 50 ml conical styrene resin test tube (Iwaki Glass), and centrifuged at 400 xg for 10 min., and the supernatant was discarded completely by suction. To the precipitated cells was added dropwise over 1 min. 1.3 ml of the PEG 4,000 solution warmed at 37° C. with gentle stirring. The cells were resuspended and dispersed by stirring for another minute. To the suspension was then added dropwise over 1 min. 1.3 ml of RPMI 1640 culture medium warmed at 37° C. After repeating the same operation once more, the cells were dispersed, by adding 9 ml of the same culture medium dropwise over 2 to 3 min. under continuous agitation. The dispersion was centrifuged at 400 xg for 10 min., and the supernatant was discarded completely by suction. To the precipitated cells was added rapidly 12.9 ml of NS-1 culture medium warmed at 37° C., and big cell clumps were then dispersed by pipetting carefully with a 10 ml pipette. The dispersion was diluted with 26 ml of the same culture medium, and distributed into 96-well microwell made of polystyrene (Iwaki Glass) so that $6.0 \times 10^5$ cells/0.1 ml exist in each well. As a preliminary treatment, the 96-well microwells had been treated with 0.2 ml of NS-1 culture medium overnight at 37° C. in a $CO_2$ incubator, and the culture medium had been removed therefrom by suction on actual use. After loaded with the cells, the microwells were subjected to cultivation at 37° C. in 7% $CO_2$/93% air under 100% humidity.

(d) Selective proliferation of hybridomas with the aid of a selective culture medium:

(1) Culture media used are as follows:

HAT selection medium: the NS-1 culture medium mentioned above in (c) supplemented with hypoxanthine (100 μM), aminopterin (0.4 μM) and thymidine (16 μM).

HT culture medium: the same composition as the HAT medium mentioned above except that aminopterin is not contained.

(2) One day after the cultivation mentioned above in (c) was started (i.e. on the first day), two drops (ca. 0.1 ml) of HAT culture medium were added with a Pasteur pipette. On the 2nd, 3rd, 5th, 8th and 11th days, the half (0.1 ml) of each culture medium was replaced with fresh HAT culture medium. On 14th day, the half of each culture medium was replaced with fresh HT culture medium. Thereafter, replacement of the half of each culture medium by fresh HT culture medium was repeated at 3 to 4 days intervals. Usually, sufficient growth of hybridoma was observed in 2 to 3 weeks. All the wells containing hybridomas grown were tested to see if there were positive wells, using a solid phase-antibody binding test (ELISA) as will be described in the subsequent (e). All the cultures with hybridomas positive in the test above were transferred to a 24-well cell well made of polystyrene (Iwaki Glass) containing 1 ml of the HT culture medium containing $10^7$ mouse thymocytes as feeders. The cultures were subjected to cultivation, as described in the preceding (c), at 37° C. in 7% $CO_2$ for about a week. Once or twice during the cultivation period, 0.5 ml of the supernatant of each well was replaced with 0.5 ml of fresh HT culture medium. At the time sufficient growth of hybridomas was observed, the cultures were checked again for the positivity by the ELISA method, and subjected to a cloning procedure by the limiting dilution method as will be explained in (f) below. The residual culture after cloning was transferred into a 25 cm² tissue culture flask made of polystyrene (Iwaki Glass), for the preparation of a frozen sample for storage.

(e) Screening for hybridomas capable of producing anti-bovine collagenase inhibitor antibody by means of the solid phase-antibody binding test (ELISA):

The method used for the present example was a slight modification of the method of Rennard et al. described in Anal. Biochem., 104, 205-214, (1980), which is appropriate for the detection of antibody production in hybridomas. Each well of a 96-well microtitration plate (Flow Laboratories, Inc.) was coated with 0.5-1.0 μg of bovine collagenase inhibitor, and the wells remaining uncoated were blocked with 1% bovine serum albumin (BSA). To the wells was added a part of the supernatant from the wells containing hybridomas grown as obtained in (d) above. The incubation was carried out at room temperature for about 1 hr. After the addition of goat anti-mouse immunoglobulin (Cappel Lab.) labeled with horseradish peroxidase as a secondary antibody, further incubation was carried out at room temperature for about 1 hr. The depth of brown color produced upon the addition of $H_2O_2$ and o-phenylenediamine as a substrate was assessed qualitatively with naked eyes or determined by measuring the absorbance at 500 nm using a Corona double wave microplate spectrophotometer (MTP-22, Corona Electric).

(f) Cloning:

In order to obtain hybridomas capable of producing monoclonal antibodies it is necessary, after the procedure mentioned above in (d), for cloning to be carried out according to the limiting dilution method, since each well can develop two or more kinds of hybridomas. A cloning culture medium containing in NS-1 culture medium $10^7$ cells per ml of mouse thymocytes as feeders was prepared. 5, 1 and 0.5/well of hybridomas were added to 36, 36 and 24 wells of a 96-well microwell, respectively. About 0.1 ml of NS-1 culture medium was further added to each well on the 5th and 12th day. About 14 to 15 days after the cloning when the sufficient growth of hybridoma could be recognized, the culture group in which more than 50% wells were negative for colony formation was subjected to ELISA. When not all of the tested wells were shown to be positive, the colonies in antibody-positive wells were enumerated and out of them 4-6 wells exhibiting the formation of one and single colony were selected for recloning. Finally, 17 hybridoma clones capable of producing monoclonal antibody to bovine collagenase inhibitor were obtained.

(g) Proliferation in vitro and in vivo of monoclonal antibody:

Monoclonal antibodies were proliferated in a conventional manner. Thus, they can be obtained from the supernatant of an appropriate culture medium such as NS-1 culture medium in which each of the resultant hybridomas were subjected to cultivation (in vitro proliferation) (The concentration of the monoclonal antibody protein 10-100 μg/ml). If a large amount of antibody is to be produced, on the other hand, an in vivo proliferation is carried out as described below. A carcinogenic excitant, Pristane (2,6,10,14-tetramethylpentadecane, Aldrich Chemical), was administered to animals (Balb/c mice) intraperitoneally in a volume of 0.5 ml per animal, which animals were of the syngenic strain as those providing the splenocytes and the myeloma cells. One to 3 weeks after the administration, 1×10⁷ cells of each hybridoma were administered intraperitoneally as above, and ascites containing 4-7 mg/ml monoclonal antibody were obtained after 1 to 2 weeks.

(h) Isotypes of monoclonal antibodies:

First of all, each of the ascites obtained in (g) above was bound to a microtitration plate coated with bovine collagenase inhibitor according to the above-described ELISA method. After washing with PBS, isotypespecific rabbit anti-mouse Ig antibodies (Zymed Laboratories) were added thereto. After washing with PBS, goat anti-rabbit IgG (H+L) antibody labeled with horseradish peroxidase, was added thereto, and 2,2'-azinodi(3-ethylbenzothiazoline sulfate-6) as a substrate and hydrogen peroxide were then added for detection. The results are shown collectively in Table 1 described hereinafter. Among the resultant monoclonal antibodies against bovine collagenase inhibitor, fifteen antibodies were found to contain immunoglobulin chain γ1/κ and one antibody γ2a/κ and one antibody γ2b/κ. (i) Purification of monoclonal antibody:

Each of the ascites obtained in the foregoing (g) was fractionated with ammonium sulfate (40% saturation) and then loaded on DEAE-Sephacel (Pharmacia) equilibrated with a 40-mM phosphate buffer solution (pH 8.0) containing 0.06-M NaCl to separate an unadsorbed fraction. This IgG fraction was gel-filtered on Sephacryl S-300 Superfine (Pharmacia) column equilibrated with a 50-mM phosphate buffer solution (pH 7.4) containing 0.42-M NaCl, whereby FCS from culture medium and mouse-derived proteins were separated and removed.

EXAMPLE 2

Reactivity between bovine dental pulp collagenase inhibitor and monoclonal antibodies
(a) Preparation of enzyme-labeled monoclonal antibodies (Fab'-POD conjugates):
(1) Preparation of Fab' fraction The IgG fraction obtained in Example 1(i) was dissolved in a 0.1-M acetate buffer solution, pH 4.2, containing 0.1-M NaCl and the solution was digested with pepsin as follows. Thus, pepsin was added to the fraction to 2% (w/w) based on the IgG therein, and the mixture was subjected to digestion at 37° C. for 24 hrs. The digested product was adjusted to a pH of 7.0 with a 2-M Tris solution thereby to stop the digestion reaction. The product was gel-filtered on a Ultrogel AcA 44 column (supplied by LKB) equilibrated with a 0.1-M phosphate buffer solution (pH 7.0) to obtain F(ab')₂ fraction.

The F(ab')₂ fraction was dialyzed against a 0.1-M phosphate buffer solution (pH 6.0) containing ethylenediamine tetraacetic acid (EDTA), and aminoethanethiol (MEA) was added to a final concentration of 10-mM to effect reduction at 37° C. for 1.5 hrs. The product was gel-filtered on a Ultrogel AcA 44 column equilibrated with a 0.1-M phosphate buffer solution (pH 6.0) containing 5-mM EDTA to obtain Fab' fraction.

(2) Preparation of maleimide-labeled POD fraction

Separately from the procedure as mentioned in (1) above, horseradish peroxidase (POD) was labeled with a maleimide compound as follows. Thus, the POD was dissolved in a 0.1-M phosphate buffer solution (pH 7.0) to 10 mg/ml and to the solution was added 25 moles, per mole of the POD, of N-(ε-maleimidocaproyloxy)succinimide (EMCS) as a solution in dimethylformamide for reaction at 30° C. for 30 min. The product was gel-filtered on a Sephadex G-50 column equilibrated with a 0.1-M phosphate buffer solution (pH 6.0) to obtain maleimide-labeled POD fraction.

(3) Preparation of Fab'-POD conjugate fraction

The fractions as prepared in (1) and (2) above were admixed so that equimolar amounts of Fab' and maleimide-labeled POD in the respective fractions were mixed. The mixture was then diluted with a 0.1-M phosphate buffer solution (pH 6.0) containing 5-mM EDTA to a final concentration, in respect of both Fab' and maleimide-labeled POD, of 100-μM. After reaction at 4° C. for 20 hrs. was added 10 moles, per mole of Fab', of N-ethylmaleimide to block unreacted thiol groups. The product was gel-filtered on a Ultrogel AcA 44 column equilibrated with a 0.1-M phosphate buffer solution (pH 6.5) to obtain Fab'-POD conjugate fraction, to which 0.1% bovine serum albumin (BSA) and 0.005% thimerosal were added for storage at 4° C.

Figure 1:
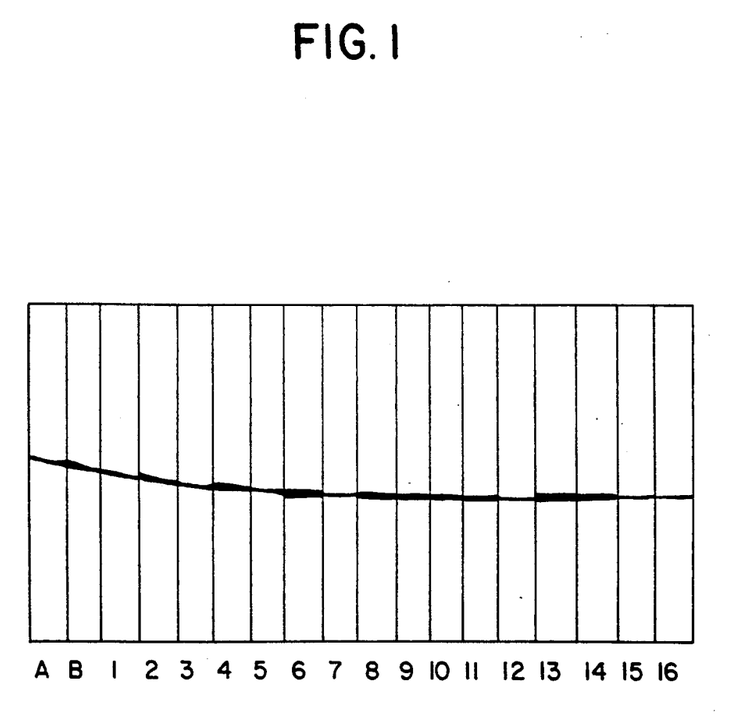
FIG. 1 shows Western blotting patterns of bovine dental pulp collagenase inhibitor subjected to SDS-PAGE, obtained with different monoclonal antibodies.

(b) Western blotting:

The bovine dental pulp collagenase inhibitor purified in Example 1(a) was subjected to SDS-PAGE and then to Western blotting, in accordance with the method of Tanabe as described in "Saibo Kogaku"(Cell Technology) 1 & 2, pp. 1061-1068 (1983), using commercially available POD-labeled goat anti-mouse immunoglobulin and the Fab'-POD conjugates obtained in Example 2(a) above, whereby patterns of enzyme antibody staining were obtained. These patterns are shown in FIG. 1. In FIG. 1, A and B show the results obtained when a nitrocellulose membrane was, subsequently to the Western blotting, immunologically stained with Fab' (clone 7-3F1)-POD and Fab' (clone 7-21B12)-POD conjugates obtained in Example 2(a), respectively.

Furthermore, numbers 1 through 16 show the results obtained when a nitrocellulose membrane was, subsequently to the Western blotting, soaked in each of the following monoclonal antibodies (all of IgG type) in solution and then immunologically stained again with POD-labeled goat anti-mouse immunoglobulin (supplied by Cappel Laboratories):

| 1: clone 7-3F1 | 2: clone 7-4F2 |
|---|---|
| 3: clone 7-5A1 | 4: clone 7-6C1 |
| 5: clone 7-7F11 | 6: clone 7-8B2 |
| 7: clone 7-9B4 | 8: clone 7-10E11 |
| 9: clone 7-11A5 | 10: clone 7-12B6 |
| 11: clone 7-15E8 | 12: clone 7-18F3 |
| 13: clone 7-19F6 | 14: clone 7-20C2 |
| 15: clone 7-21B12 | 16: clone 7-23G9. |

As it is evident from FIG. 1, all the monoclonal antibodies mentioned above were found to have reactivity with bovine dental pulp collagenase inhibitor.

EXAMPLE 3

Sandwich enzyme immunoassay
(a) Preparation of monoclonal antibody-coated balls:

According to the method of Ishikawa et al. as described in J. Immunoassay 4, 209-327 (1983), monoclonal antibody obtained in Example 1(i) was dissolved in a 0.1-M phosphate buffer solution (pH 7.5) containing 0.1% sodium azide. The monoclonal antibody solution was adjusted to a concentration of 100 μg/ml ($A_{280}$=0.15) and polystyrene balls (6.5 mm in diameter, supplied by Precision Plastic Ball) were soaked therein and allowed to stand at 4° C. for 24 hrs. After removal of the monoclonal antibody solution, the balls were washed five times with a 10-mM phosphate buffer solution (pH 7.0) containing 0.1% BSA, 0.1% NaCl and 0.1% sodium azide (hereinafter referred to Buffer A for short), and then soaked in Buffer A for storage at 4° C.

(b) Sandwich assay:

A solution of purified collagenase inhibitor or a sample solution containing collagenase inhibitor was diluted with Buffer A containing 1% BSA and a 300 μl aliquot of dilution was placed in each test tube. After addition of an antibody-coated ball prepared in (a) above, the test tube was warmed at 30° C. for 1 hr. with shaking (first reaction) and then washed three times with 3 ml portions each of a 10-mM phosphate buffer solution (pH 7.0) containing 0.1-M NaCl. The Fab'-POD conjugate prepared in Example 2(a) was diluted to 20 ng/tube with a 10-mM phosphate buffer solution (pH 7.0) containing 0.1% BSA and 0.1-M NaCl, and then warmed at 30° C. for 1 hr. with shaking (second reaction). After the reaction was complete, washing was carried out in the same manner as upon the completion of the first reaction. 0.3 ml of a substrate for POD dissolved in a 0.1-M acetate buffer solution (pH 5.5), i.e. 0.0134% tetramethylbenzidine (TMBZ) was added. After further addition of 0.1 ml of 0.01% hydrogen peroxide, the mixture was warmed at 30° C. for 1 hr. with shaking (third reaction), whereafter the reaction was stopped by the addition of 0.6 ml of 1.33N sulfuric acid. The $A_{450}$ value of the reaction mixture was measured on a spectrophotometer and the amount of collagenase inhibitor in the sample was determined from a standard curve.

Figure 2:
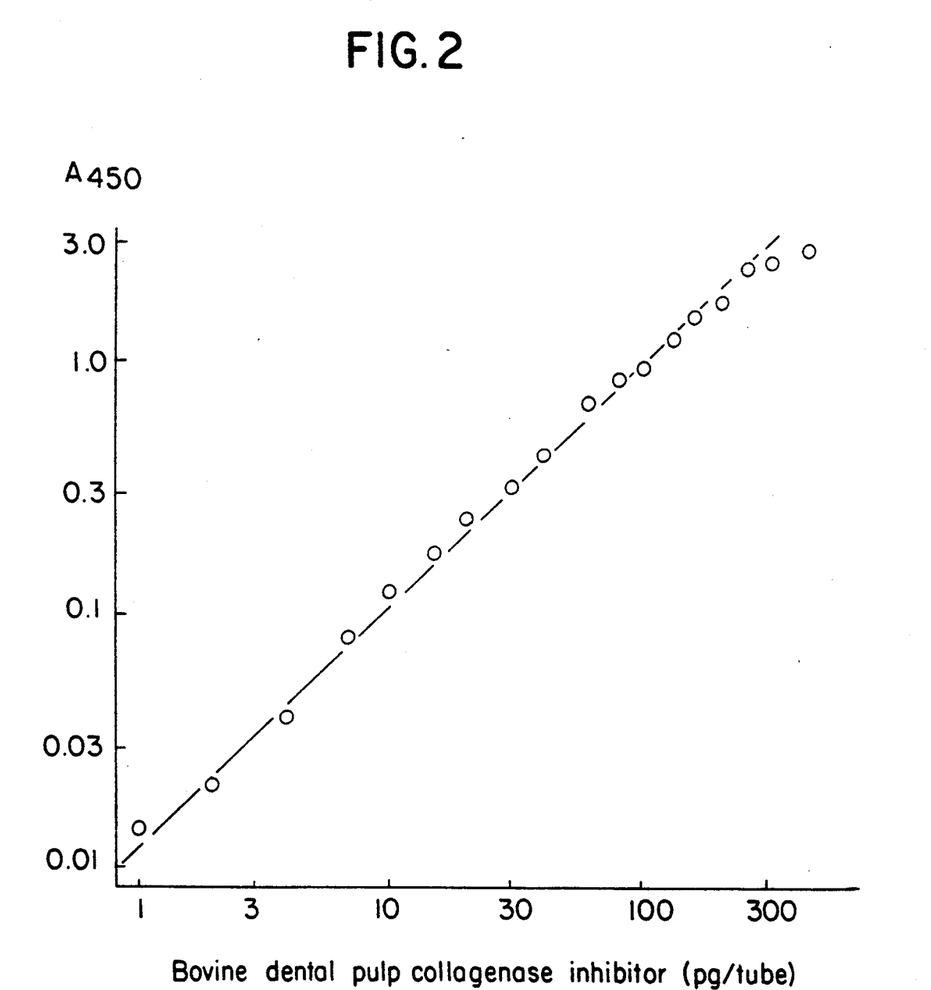
FIG. 2 shows a standard curve for bovine dental pulp collagenase inhibitor, prepared with a solid phase 7-23G9 antibody-conjugate Fab'(7-6C1)-POD assay system.

(c) Screening for monoclonal antibodies for use in sandwich assay:

In order to screen for monoclonal antibody combinations with which the quantitation of collagenase inhibitor is possible, Fab'-POD conjugate was prepared from each of the following monoclonal antibodies purified by the method as used in Example 1(i): clone 7-3F1; 7-6C1; 7-19F6 and 7-21B12. Using 1 ng/tube of purified bovine dental pulp collagenase inhibitor was carried out a quantitative sandwich assay, according to the method as used in Example 3(b), with each of the following monoclonal antibodies as solid phase: clone 7-3F1; 7-4F2; 7-5A1; 7-6C1; 7-7F11, 7-8B2; 7-9B4; 7-10E11; 7-11A5; 7-12B6; 7-15E8; 7-18F3; 7-19F6; 7-20C2; 7-21B12 and 7-23G9. The resultant $A_{450}$ values are shown in Table 2 below. It is to be noted the $A_{450}$ values in Table 2 are those obtained by subtracting values for sandwich assay in which no collagenase inhibitor was added from those for sandwich assay in which 1 ng of sample was added. All the four different Fab'-POD conjugates mentioned above were found to show $A_{450}$ values not smaller than 2 for any of the six different antibodies as solid phase: 7-4F2; 7-11A5; 7-12B6; 7-18F3; 7-20C2 and 7-23G9. A quantitative sandwich assay was further carried out by using different amounts of bovine dental pulp collagenase inhibitor added for each of these twenty four combinations. The results obtained when Fab' (clone 7-6C1)-POD conjugate was used in combination with clone 7-23G9 antibody as the solid phase are shown in FIG. 2. As is shown by FIG. 2, linearity was obtained between the amount of bovine dental pulp collagenase inhibitor added and $A_{450}$, the determination sensitivities being about 1 pg (32 a mol) per tube. Such linearity was also observed with combinations other than the one mentioned above, it being thereby established that quantitative sandwich assay is possible with any of the combinations.

EXAMPLE 4

Identification of collagenase inhibitor in human serum (a) Preparation of Affinity column:

In accordance with the method as described by Axén et al. in Nature 214, 1302–1304 (1967) and by Cuatrecasas et al. in Proc. Natl. Acad. Sci. USA, 61, 636–643 (1968), purified monoclonal antibody obtained in Example 1(i) was immobilized as ligand onto a Sepharose 4B support by way of the use of cyanogen bromide. The resultant antibody-Sepharose 4B gel (0.3 ml) was then filled into a glass column and equilibrated, before use, with a 30-mM Tris-HCl buffer solution (pH 8.0) containing 0.1-M NaCl and 5-mM $CaCl_2$.

Figure 3:
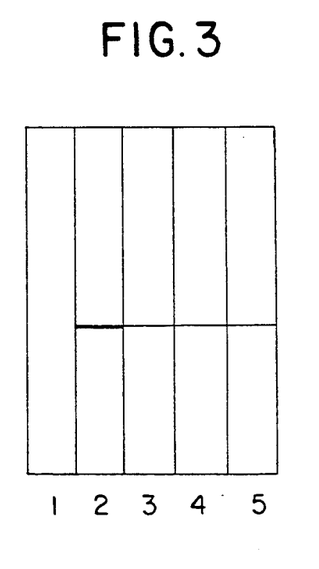
FIG. 3 shows immunologically stained patterns obtained by subjecting human serum collagenase inhibitor to SDS-PAGE and then to Western blotting.

(b) Affinity column chromatography for human serum collagenase inhibitor:

Human serum (1 ml) was dialyzed against a 30 mM Tris-HCl buffer solution (pH 8.0) containing 0.1-M NaCl and 5-mM $CaCl_2$ and then applied onto a clone 7-21B12 antibody-Sepharose 4B column as prepared in accordance with the manner mentioned in (a) above. The column was washed with the same buffer as above to obtain "unadsorbed fraction". It was then washed with a 30-mM Tris-HCl buffer solution (pH 7.5) containing 2-M NaCl and subsequently with a 0.2-M glycine-NaOH buffer solution (pH 10.5) containing 0.5-M NaCl to obtain "washed fraction". Protein adsorbed on the column was finally eluted with a 0.2-M glycine-HCl buffer solution (pH 2.0) to obtain "eluted fraction". The thus obtained eluted fraction was dialyzed against a 30-mM Tris-HCl buffer solution (pH 8.0) containing 0.1-M NaCl and 5-mM $CaCl_2$, and then subjected again to affinity chromatography on a clone 7-21B12 antibody-Sepharose 4B column to repeat the same procedure as described above, whereby collagenase inhibitor was obtained in the eluted fraction. In order to test whether the monoclonal antibodies against bovine dental pulp collagenase inhibitor react with human serum collagenase inhibitor, the eluted fraction mentioned above was subjected to SDS-PAGE and then to Western blotting. FIG. 3 shows the results obtained when a nitrocellulose membrane was, subsequently to the Western blotting, immunologically stained with Fab'-POD conjugate prepared from each of the following monoclonal antibodies: 1, clone 7-3F1; 2, clone 7-6C1; 3, clone 7-19F6; 4, clone 7-21B12; and 5, clone 7-23G9. As is shown in FIG. 3, collagenase inhibitors with reactivity with monoclonal antibody against bovine dental pulp collagenase inhibitor were found to exist in human serum. On top of that, it has also been found that the molecular weight of each of these collagenase inhibitors was the same as that (32,000D) of bovine dental pulp collagenase inhibitor obtained in Example 1(a).

EXAMPLE 5

Quantitative determination of collagenase inhibitor in human serum by sandwich assay (a) Preparation of standard curve:

Screening was performed for the most suitable monoclonal antibody combination for conducting sandwich assay for human collagenase inhibitor. Thus, as shown in Example 3(c), twenty four combinations between four different Fab'-POD conjugates, i.e. Fab'(7-3F1)-POD, Fab'(7-6C1)-POD, Fab'(7-19F6)-POD and Fab'(7-21B12)-POD, and 6 different monoclonal antibodies as solid phase antibodies, i.e. clones 7-4F2, 7-

Figure 4:
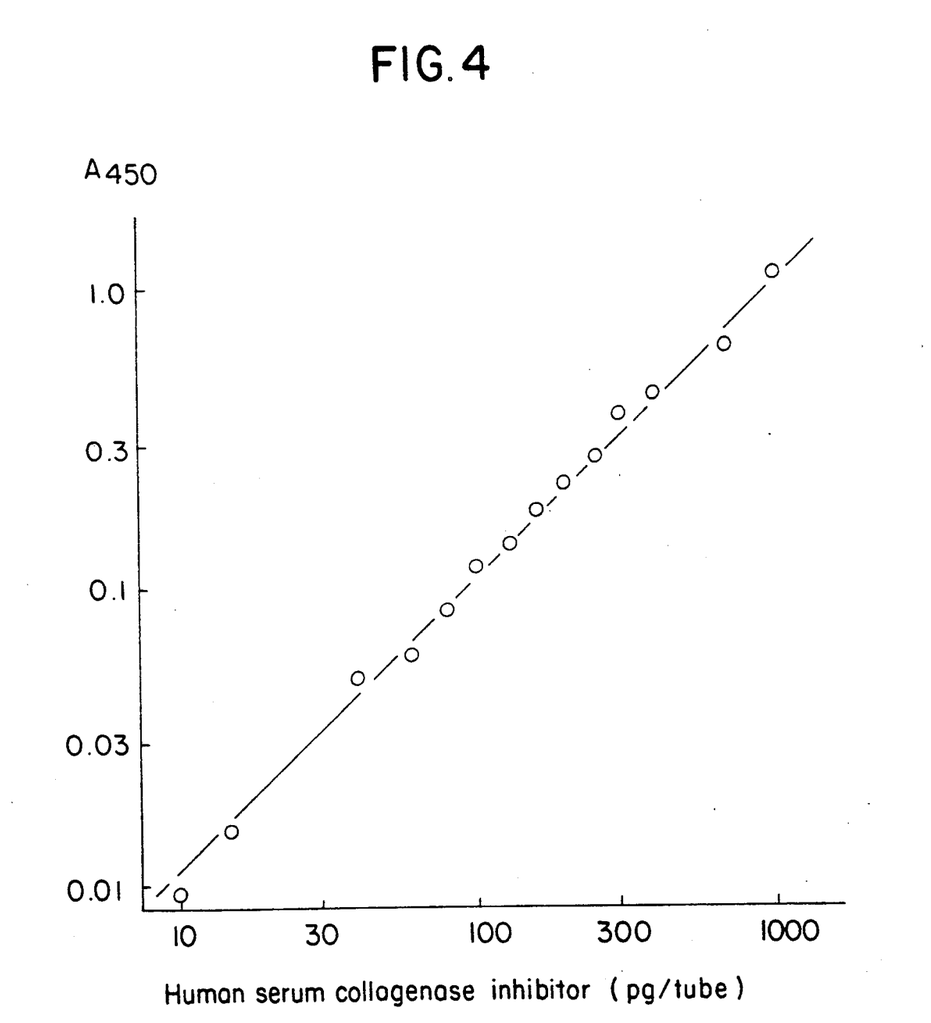
FIG. 4 shows a standard curve for human serum collagenase inhibitor, prepared with a solid phase 7-23G9 antibody-conjugate Fab'(7-6C1)-POD assay system.

11A5, 7-12B6, 7-18F3, 7-20C2 and 7-23G9, were screened for those with which quantitative determination of human serum collagenase inhibitors treated by column chromatography in the manner as described in Example 4(b) is possible. As a result, when human serum collagenase inhibitor was used as antigen, no $A_{450}$ signals were detected for most of the combinations used. It has been found, however, that quantitative sandwich assay is possible with the combination of clone 7-23G9 antibody as the solid phase antibody and Fab'(clone 7-6C1)-POD as the conjugate. A standard curve was prepared by performing the quantitative sandwich assay in accordance with the method as described in Example 3(c) with varied amounts of human serum collagenase inhibitor added, using the combination mentioned above. The results thus obtained are shown in FIG. 4. As is shown by FIG. 4, linearity is attained between the amount of human serum collagenase inhibitor added and $A_{450}$, it being thereby found that quantitative determination of human collagenase inhibitor is possible. The determination sensitivity, however, was found to be about 10 pg (320 a mol) per tube, ten times lower than that (i.e. 1 pg per tube) for bovine dental pulp collagenase inhibitor.

(b) Quantitative determination of collagenase inhibitor in sera of patients:

Using the monoclonal antibody combination specified in (a) above, ninety-five serum samples from normal subjects, one hundred from patients with hepatocellular carcinoma, and three from those with metastatic liver carcinoma were sandwich-assayed quantitatively for collagenase inhibitor contained therein. The results are shown in Tables 3-1, 3-2 and 3-3, respectively. In this sandwich assay, there was used the human serum collagenase inhibitor purified in Example 4(b) as the antigen for the preparation of the standard curve. This quantitation was performed with the serum samples diluted 1,600 times with Buffer A containing 1% BSA. The values indicated in Tables 3-1 and 3-2 are expressed as means of duplicate experiments. As is seen from Tables 3-2 and 3-3, the mean amounts of collagenase inhibitor present in one ml of serum from patients with hepatocellular carcinoma and from those with metastatic liver carcinoma were as high as $3.22 \pm 2.10$ μg and $7.81 \pm 3.87$ μg, respectively, whereas as is seen from Table 3-1 that from normal subjects was $1.59 \pm 0.37$ μg. Forty-six, forty-five and twenty-six serum samples from patients with liver cirrhosis, with chronic active hepatitis and with chronic inactive hepatitis, respectively, were sandwich-assayed quantitatively and the values obtained with the respective samples are shown in Tables 4-1, 4-2 and 4-3. As a result, the mean amounts of collagenase inhibitor in sera of patients with liver cirrhosis, with chronic active hepatitis and with chronic inactive hepatitis were $1.52 \pm 1.08$ μg, $1.55 \pm 0.58$ μg and $1.10 \pm 0.48$ μg, respectively, all showing no significant difference as compared to the serum collagenase inhibitor level for normal subjects.

EXAMPLE 6

Purification of human serum collagenase inhibitor

Figure 5:
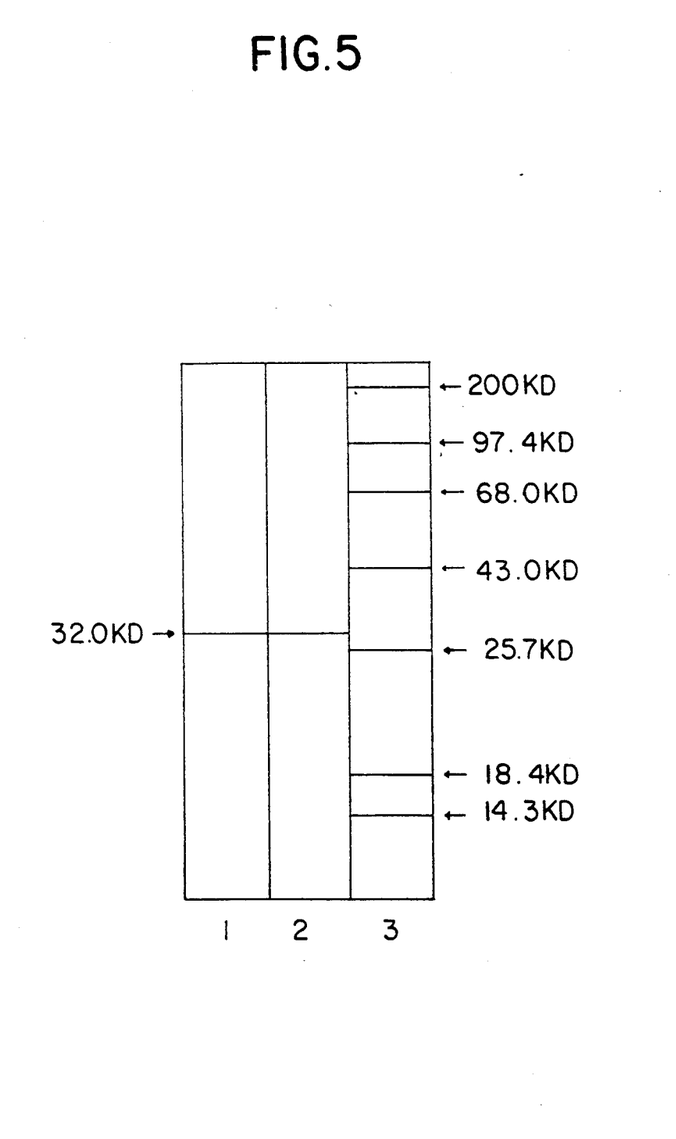
FIG. 5 shows SDS-PAGE patterns of collagenase inhibitor purified from human sera.

As mentioned above, in the eluted fraction finally obtained in Example 4(b) is present collagenase inhibitor with reactivity with monoclonal antibodies against bovine dental pulp collagenase inhibitor (see FIG. 3). A variety of proteins, however, were observed to exist therein, in addition to the collagen inhibitor, which do not react with the monoclonal antibodies mentioned above. Based on this observation, the eluted fraction was gel-filtered on an AcA 44 column equilibrated with a 0.1-M phosphate buffer solution (pH 7.5) for separation of collagenase inhibitor from other proteins thereby to purify human serum collagenase inhibitor. FIG. 5 shows the respective SDS-PAGE patterns for the resultant serum collagenase inhibitor (1), bovine dental pulp collagenase inhibitor (2) as a control and molecular weight markers (3). As is seen in FIG. 5, the molecular weight of human serum collagenase inhibitor was found to be the same as that (i.e. 32,000D) of bovine dental pulp collagenase inhibitor.

EXAMPLE 7

Figure 6:
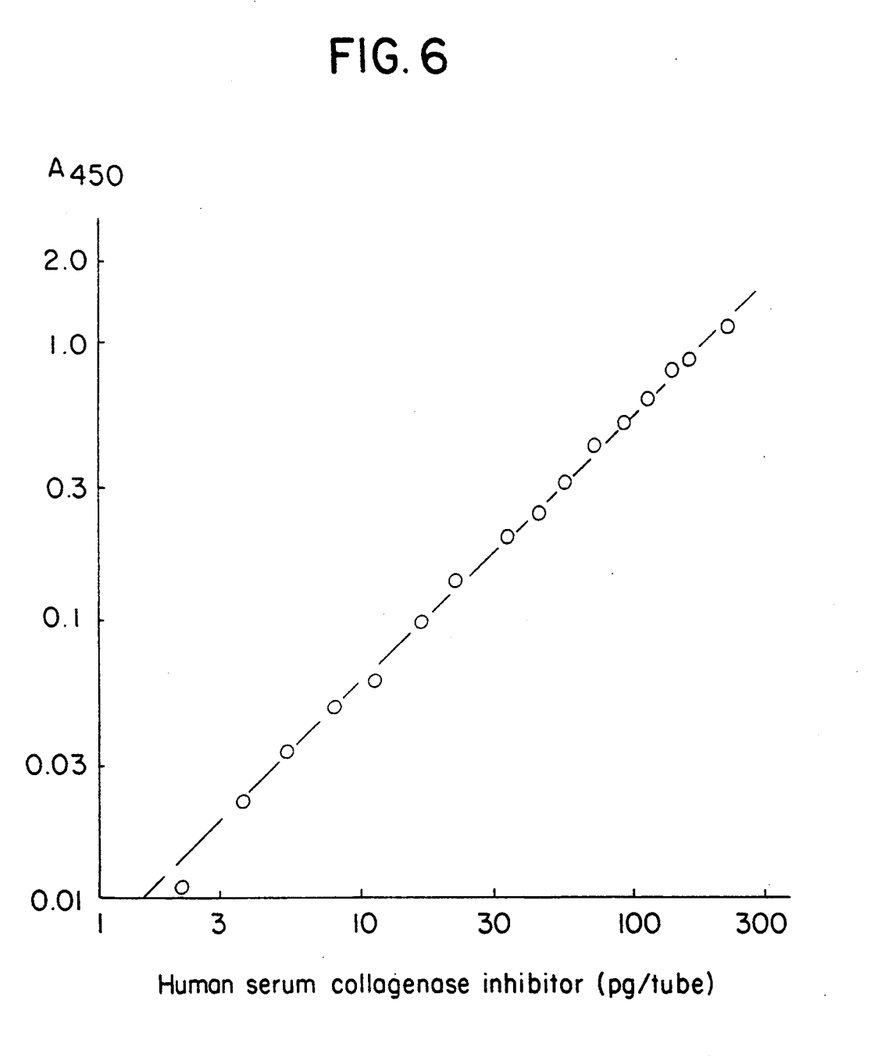
FIG. 6 shows a standard curve prepared by sandwich assay for purified human serum collagenase inhibitor.

Preparation of standard curves by sandwich assay for purified human serum collagenase inhibitor A standard curve was prepared by performing the sandwich assay quantitatively with varied amounts of the purified human serum collagenase inhibitor obtained in Example 6 added, using the monoclonal antibody combination as mentioned in Example 5(a). The results thus obtained are shown in FIG. 6. As is seen from FIG. 6, linearity is attained between the amount of human serum collagenase inhibitor added and $A_{450}$, the determination sensitivity being 1.5 pg (48 a mole) per tube. This determination sensitivity was found to be 6.7 times higher than in the case of the standard curve prepared in Example 5(a) and 1.5 times lower than that for bovine dental pulp collagenase inhibitor as described in Example 3(c).

EXAMPLE 8

Diagnosis of hepatic carcinoma by way of quantitation of collagenase inhibitor in human sera or plasmas by sandwich assay (a) Quantative determination of collagenase inhibitor in sera from patients with liver disorders:

Using the monoclonal antibody combination as mentioned in Example 7, fifty serum samples from normal subjects, one hundred from patients with hepatocellular carcinoma and three from those with metastatic liver carcinoma were sandwich-assayed quantitatively for collagenase inhibitor contained therein. The results are shown in Tables 5-1, 5-2 and 5-3, respectively. In this sandwich assay there was used the human serum collagenase inhibitor purified in Example 6 as the antigen for preparation of the standard curve. This quantification was performed with the serum samples diluted 1,600 times with Buffer A containing 1% BSA. The values indicated in Tables 5-1, 5-2 and 5-3 are expressed as means of duplicate experiments. As is seen from Tables 5-2 and 5-3, the mean amounts of collagenase inhibitor present in one ml of serum from patients with hepatocellular carcinoma and from those with metastatic liver carcinoma were as high as $484 \pm 316$ ng and $1171 \pm 712$ ng, respectively, whereas as is seen from Table 5-1 that from normal subjects was $184 \pm 31$ ng. Forty-six, forty-five and twenty-six serum samples from patients with liver cirrhosis, with chronic active hepatitis and with chronic inactive hepatitis, respectively, were sandwich-assayed quantitatively and the values obtained with the respective samples are shown in Tables 6-1, 6-2 and 6-3. As shown in these tables, the mean amounts of collagenase inhibitor in sera of patients with liver cirrhosis, with chronic active hepatitis and with chronic inactive hepatitis were $228 \pm 163$ ng, $233 \pm 88$ ng and $166 \pm 73$ ng, respectively, all showing no significant difference as compared to the serum collagenase inhibitor level for normal subjects.

(b) Quantitative determination of collagenase inhibitor in plasmas from patients with liver disorders:

In accordance with the method of Ludlam and Cash as described in Br. J. Haematol. 33, 239-247 (1976), plasma was taken from bloods of normal subjects and of patients with hepatocellular carcinoma. The plasma thus taken is the supernatant obtained from centrifugation at 1,900 x g for 60 min. at 4° C. of cooled blood supplemented with EDTA, prostaglandin $E_1$ and theophylline, wherein the platelets in the blood are retained in the precipitated fraction without decomposition.

The thus obtained twenty-six plasma samples from normal subjects and eight from patients with hepatocellular carcinoma were sandwich-assayed quantitatively for collagenase inhibitor present therein by the same method as in (a) above. The results are shown in Table 7 below. As is seen from Table 7, the mean amount of collagenase inhibitor present in one ml of plasma from patients with hepatocellular carcinoma was as high as 583±447 ng, whereas that from normal subjects was 64±10 ng.

Figure 7:
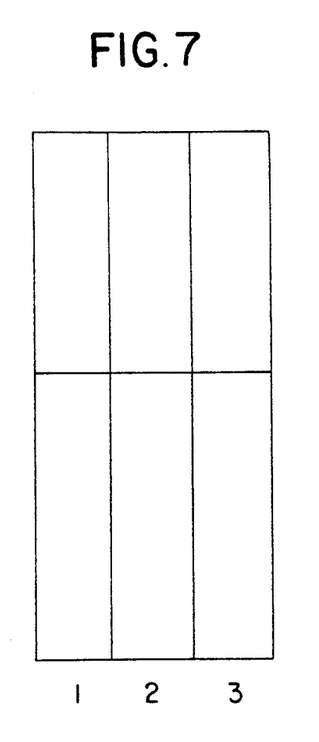
FIG. 7 shows Western blotting patterns obtained when the eluted fraction obtained upon application of human sera onto an affinity column with IgG(7-23G9) antibody bound was subjected to SDS-PAGE followed by application of Fab'(7-6C1)-POD conjugate.

(c) Confirmation of specific reactivity between monoclonal antibody and collagenase inhibitor:

As was demonstrated in Example 4(b), the two monoclonal antibodies (clone 7-6C1 and clone 7-23G9) used in the sandwich assay exhibit reactivity with human collagenase inhibitor. A test was performed to establish that these monoclonal antibodies specifically react with collagenase inhibitor in such systems as sera, plasmas and synovial fluids in which different proteins are present dissolved in high concentrations. The sera from normal subjects and from patients with hepatic carcinoma were diluted five times with a 30-mM Tris-HCl buffer solution (pH 8.0) containing 0.1-M NaCl and 5-mM $CaCl_2$, and then applied onto Sepharose 4B column with immobilized clone 7-23G9 (antibody as the solid phase for the sandwich assay) which is prepared as described in Example 4(a) to obtain the eluted fraction according to the manner as described in Example 4(b). After being subjected to SDS-PAGE followed by Western blotting, the eluted fraction was immunologically stained with Fab'(clone 7-6C1)-POD conjugate, a labeled antibody for the sandwich assay. The results are shown in FIG. 7. As seen from FIG. 7, a single band was shown for all the cases (1: purified human serum collagenase inhibitor; 2: sera from normal subjects; and 3: sera from patients with hepatic carcinoma). It has thus been demonstrated that according to the sandwich assay in the method of diagnosis of the invention collagenase inhibitor is determined extremely specifically.

As is apparent from the foregoing description, it is possible, with the method of the present invention, to perform the diagnosis of hepatic carcinoma straightforwardly in a short period of time with high sensitivity.

TABLE 1

| Clone No. | Subclass/Chain |
|---|---|
| 7-3F1 | IgG1/κ |
| 7-4F2 | IgG1/κ |
| 7-5A1 | IgG1/κ |
| 7-6C1 | IgG1/κ |
| 7-7F11 | IgG1/κ |
| 7-8B2 | IgG2a/κ |
| 7-9B4 | IgG1/κ |
| 7-10E11 | IgG1/κ |
| 7-11A5 | IgG1/κ |
| 7-12B6 | IgG1/κ |
| 7-14E9 | IgG1/κ |
| 7-15E8 | IgG1/κ |
| 7-18F3 | IgG2b/κ |
| 7-19F6 | IgG1/κ |
| 7-20C2 | IgG1/κ |
| 7-21B12 | IgG1/κ |
| 7-23G9 | IgG1/κ |

TABLE 2

| Solid Phase Antibody | Fab'-POD Conjugate | | | |
|---|---|---|---|---|
| | IgG1 (7-3F1) | IgG1 (7-6C1) | IgG1 (7-19F6) | IgG1 (7-21B12) |
| IgG1 (7-3F1) | 0.011 | 3.989 | 2.252 | 2.684 |
| IgG1 (7-4F2) | 3.144 | 4.811 | 3.354 | 3.083 |
| IgG1 (7-5A1) | 3.257 | 0.010 | 0 | 0 |
| IgG1 (7-6C1) | 2.152 | 0.001 | 0.011 | 0 |
| IgG1 (7-7F11) | 0.125 | 0.239 | 0.102 | 0.067 |
| IgG2a (7-8B2) | 0 | 3.967 | 1.064 | 1.288 |
| IgG1 (7-9B4) | 0.196 | 0.057 | 0.029 | 0.020 |
| IgG1 (7-10E11) | 0.891 | 0.007 | 0.001 | 0.002 |
| IgG1 (7-11A5) | 3.406 | 4.455 | 3.288 | 3.260 |
| IgG1 (7-12B6) | 3.604 | 4.083 | 2.952 | 3.077 |
| IgG1 (7-15E8) | 0.313 | 0.781 | 0.387 | 1.897 |
| IgG2b (7-18F3) | 3.362 | 4.735 | 3.114 | 3.021 |
| IgG1 (7-19F6) | 1.066 | 0 | 0 | 0.004 |
| IgG1 (7-20C2) | 3.277 | 4.553 | 3.355 | 3.240 |
| IgG1 (7-21B12) | 2.107 | 0.002 | 0.003 | 0 |
| IgG1 (7-23G9) | 3.622 | 4.386 | 3.027 | 3.092 |

TABLE 3 - 1

| Sera from normal subjects | |
|---|---|
| Sample No. | Collagenase inhibitor (μg/ml) |
| 1 | 1.57 |
| 2 | 2.60 |
| 3 | 1.81 |
| 4 | 1.41 |
| 5 | 1.57 |
| 6 | 1.69 |
| 7 | 1.84 |
| 8 | 2.00 |
| 9 | 1.92 |
| 10 | 1.14 |
| 11 | 1.61 |
| 12 | 1.49 |
| 13 | 2.05 |
| 14 | 2.00 |
| 15 | 2.12 |
| 16 | 1.41 |
| 17 | 1.22 |
| 18 | 1.57 |
| 19 | 2.36 |
| 20 | 1.97 |
| 21 | 1.18 |
| 22 | 2.12 |
| 23 | 1.41 |

TABLE 3 - 1-continued

Sera from normal subjects

| Sample No. | Collagenase inhibitor (μg/ml) |
| --- | --- |
| 24 | 1.53 |
| 25 | 2.08 |
| 26 | 1.49 |
| 27 | 1.02 |
| 28 | 1.73 |
| 29 | 1.82 |
| 30 | 1.14 |
| 31 | 1.81 |
| 32 | 1.49 |
| 33 | 1.81 |
| 34 | 1.41 |
| 35 | 1.61 |
| 36 | 1.49 |
| 37 | 1.02 |
| 38 | 2.43 |
| 39 | 1.73 |
| 40 | 1.73 |
| 41 | 1.49 |
| 42 | 1.69 |
| 43 | 1.46 |
| 44 | 1.69 |
| 45 | 0.89 |
| 46 | 1.22 |
| 47 | 1.41 |
| 48 | 1.22 |
| 49 | 1.18 |
| 50 | 1.49 |
| 51 | 1.57 |
| 52 | 1.41 |
| 53 | 1.14 |
| 54 | 1.30 |
| 55 | 1.69 |
| 56 | 1.49 |
| 57 | 1.53 |
| 58 | 2.43 |
| 59 | 1.84 |
| 60 | 1.77 |
| 61 | 2.08 |
| 62 | 1.61 |
| 63 | 1.37 |
| 64 | 2.05 |
| 65 | 1.73 |
| 66 | 1.37 |
| 67 | 0.94 |
| 68 | 1.61 |
| 69 | 1.06 |
| 70 | 1.61 |
| 71 | 0.89 |
| 72 | 1.41 |
| 73 | 2.05 |
| 74 | 1.57 |
| 75 | 1.14 |
| 76 | 1.22 |
| 77 | 1.49 |
| 78 | 1.57 |
| 79 | 1.02 |
| 80 | 1.60 |
| 81 | 1.65 |
| 82 | 2.32 |
| 83 | 1.94 |
| 84 | 1.57 |
| 85 | 1.14 |
| 86 | 1.73 |
| 87 | 1.37 |
| 88 | 1.49 |
| 89 | 1.18 |
| 90 | 1.22 |
| 91 | 1.41 |
| 92 | 1.06 |
| 93 | 2.32 |
| 94 | 2.36 |
| 95 | 1.46 |
| Mean 1.59 ± 0.37 μg/ml | |

TABLE 3 - 2

Sera from patients with hepatocellular carcinoma

| Sample No. | Collagenase inhibitor (μg/ml) |
| --- | --- |
| 1 | 3.38 |
| 2 | 2.28 |
| 3 | 2.35 |
| 4 | 4.25 |
| 5 | 4.32 |
| 6 | 4.10 |
| 7 | 1.34 |
| 8 | 4.32 |
| 9 | 0.94 |
| 10 | 7.39 |
| 11 | 3.07 |
| 12 | 3.67 |
| 13 | 13.77 |
| 14 | 3.61 |
| 15 | 4.32 |
| 16 | 4.17 |
| 17 | 2.04 |
| 18 | 1.37 |
| 19 | 1.46 |
| 20 | 1.53 |
| 21 | 5.59 |
| 22 | 1.89 |
| 23 | 1.80 |
| 24 | 2.28 |
| 25 | 2.16 |
| 26 | 7.08 |
| 27 | 1.58 |
| 28 | 4.53 |
| 29 | 3.07 |
| 30 | 5.83 |
| 31 | 2.91 |
| 32 | 11.40 |
| 33 | 3.93 |
| 34 | 4.72 |
| 35 | 2.24 |
| 36 | 2.44 |
| 37 | 1.85 |
| 38 | 5.35 |
| 39 | 3.70 |
| 40 | 1.18 |
| 41 | 2.99 |
| 42 | 4.56 |
| 43 | 1.65 |
| 44 | 1.70 |
| 45 | 1.65 |
| 46 | 1.22 |
| 47 | 1.80 |
| 48 | 1.34 |
| 49 | 1.34 |
| 50 | 1.37 |
| 51 | 1.53 |
| 52 | 4.17 |
| 53 | 2.83 |
| 54 | 2.13 |
| 55 | 4.87 |
| 56 | 5.27 |
| 57 | 7.08 |
| 58 | 8.66 |
| 59 | 4.65 |
| 60 | 2.91 |
| 61 | 4.17 |
| 62 | 1.58 |
| 63 | 4.48 |
| 64 | 5.83 |
| 65 | 2.91 |
| 66 | 3.38 |
| 67 | 4.63 |
| 68 | 1.46 |
| 69 | 1.89 |
| 70 | 4.10 |
| 71 | 1.46 |
| 72 | 2.98 |
| 73 | 2.99 |
| 74 | 1.37 |
| 75 | 1.65 |
| 76 | 2.32 |
| 77 | 1.58 |

TABLE 3 - 2-continued

Sera from patients with hepatocellular carcinoma

| Sample No. | Collagenase inhibitor (μg/ml) |
|---|---|
| 78 | 5.27 |
| 79 | 2.44 |
| 80 | 2.13 |
| 81 | 1.65 |
| 82 | 2.91 |
| 83 | 2.91 |
| 84 | 6.76 |
| 85 | 0.82 |
| 86 | 2.32 |
| 87 | 1.85 |
| 88 | 2.99 |
| 89 | 2.24 |
| 90 | 2.91 |
| 91 | 2.49 |
| 92 | 2.09 |
| 93 | 1.53 |
| 94 | 2.16 |
| 95 | 3.46 |
| 96 | 1.10 |
| 97 | 1.97 |
| 98 | 1.46 |
| 99 | 3.86 |
| 100 | 3.22 |
| Mean 3.22 ± 2.10 μg/ml | |

TABLE 3 - 3

Sera from patients with metastatic liver carcinoma

| Sample No. | Collagenase inhibitor (μg/ml) |
|---|---|
| 1 | 13.01 |
| 2 | 6.69 |
| 3 | 3.72 |
| Mean 7.81 ± 3.87 μg/ml | |

TABLE 4-1

Sera from patients with liver cirrhosis

| Sample No. | Collagenase inhibitor (μg/ml) |
|---|---|
| 1 | 1.22 |
| 2 | 0.75 |
| 3 | 0.77 |
| 4 | 1.14 |
| 5 | 1.22 |
| 6 | 1.37 |
| 7 | 1.03 |
| 8 | 1.77 |
| 9 | 1.58 |
| 10 | 1.65 |
| 11 | 1.70 |
| 12 | 2.13 |
| 13 | 1.06 |
| 14 | 0.89 |
| 15 | 2.32 |
| 16 | 2.44 |
| 17 | 2.12 |
| 18 | 1.42 |
| 19 | 1.53 |
| 20 | 1.70 |
| 21 | 2.52 |
| 22 | 0.25 |
| 23 | 7.63 |
| 24 | 1.22 |
| 25 | 2.11 |
| 26 | 0.82 |
| 27 | 1.85 |
| 28 | 2.00 |
| 29 | 2.12 |
| 30 | 0.67 |
| 31 | 1.42 |

TABLE 4-1-continued

Sera from patients with liver cirrhosis

| Sample No. | Collagenase inhibitor (μg/ml) |
|---|---|
| 32 | 0.80 |
| 33 | 1.03 |
| 34 | 1.70 |
| 35 | 0.64 |
| 36 | 0.94 |
| 37 | 2.12 |
| 38 | 0.57 |
| 39 | 0.34 |
| 40 | 1.49 |
| 41 | 1.80 |
| 42 | 0.79 |
| 43 | 1.42 |
| 44 | 0.66 |
| 45 | 1.49 |
| 46 | 1.49 |
| Mean 1.52 ± 1.07 μg/ml | |

TABLE 4 - 2

Sera from patients with chronic active hepatitis

| Sample No. | Collagenase inhibitor (μg/ml) |
|---|---|
| 1 | 1.42 |
| 2 | 2.59 |
| 3 | 1.41 |
| 4 | 3.38 |
| 5 | 1.37 |
| 6 | 1.03 |
| 7 | 1.77 |
| 8 | 1.61 |
| 9 | 1.42 |
| 10 | 1.89 |
| 11 | 1.85 |
| 12 | 1.80 |
| 13 | 1.65 |
| 14 | 1.22 |
| 15 | 1.85 |
| 16 | 0.97 |
| 17 | 0.76 |
| 18 | 2.04 |
| 19 | 2.09 |
| 20 | 2.16 |
| 21 | 1.89 |
| 22 | 1.65 |
| 23 | 1.25 |
| 24 | 1.77 |
| 25 | 1.65 |
| 26 | 1.92 |
| 27 | 0.86 |
| 28 | 2.91 |
| 29 | 1.37 |
| 30 | 1.15 |
| 31 | 1.30 |
| 32 | 2.24 |
| 33 | 1.10 |
| 34 | 0.76 |
| 35 | 0.72 |
| 36 | 0.72 |
| 37 | 1.97 |
| 38 | 0.91 |
| 39 | 1.06 |
| 40 | 1.97 |
| 41 | 0.91 |
| 42 | 1.77 |
| 43 | 0.91 |
| 44 | 1.85 |
| 45 | 0.91 |
| Mean 1.55 ± 0.58 μg/ml | |

TABLE 4 - 3

Sera from patients with chronic inactive hepatitis

| Sample No. | Collagenase inhibitor (μg/ml) |
|---|---|
| 1 | 1.58 |
| 2 | 1.30 |
| 3 | 1.10 |
| 4 | 1.06 |
| 5 | 0.97 |
| 6 | 1.37 |
| 7 | 0.72 |
| 8 | 1.34 |
| 9 | 1.34 |
| 10 | 1.15 |
| 11 | 1.85 |
| 12 | 2.68 |
| 13 | 1.18 |
| 14 | 1.15 |
| 15 | 1.18 |
| 16 | 1.46 |
| 17 | 0.49 |
| 18 | 0.54 |
| 19 | 0.30 |
| 20 | 1.15 |
| 21 | 0.79 |
| 22 | 0.52 |
| 23 | 0.63 |
| 24 | 0.98 |
| 25 | 0.91 |
| 26 | 0.97 |
| Mean 1.10 ± 0.48 μg/ml | |

TABLE 5 - 1

Sera from normal subjects

| Sample No. | Collagenase inhibitor (ng/ml) |
|---|---|
| 1 | 123 |
| 2 | 131 |
| 3 | 210 |
| 4 | 161 |
| 5 | 176 |
| 6 | 210 |
| 7 | 200 |
| 8 | 191 |
| 9 | 155 |
| 10 | 210 |
| 11 | 155 |
| 12 | 200 |
| 13 | 170 |
| 14 | 210 |
| 15 | 123 |
| 16 | 139 |
| 17 | 155 |
| 18 | 161 |
| 19 | 176 |
| 20 | 200 |
| 21 | 221 |
| 22 | 200 |
| 23 | 170 |
| 24 | 221 |
| 25 | 150 |
| 26 | 155 |
| 27 | 225 |
| 28 | 185 |
| 29 | 245 |
| 30 | 200 |
| 31 | 210 |
| 32 | 210 |
| 33 | 176 |
| 34 | 165 |
| 35 | 176 |
| 36 | 176 |
| 37 | 185 |
| 38 | 245 |
| 39 | 155 |
| 40 | 210 |
| 41 | 155 |

TABLE 5 - 1-continued

Sera from normal subjects

| Sample No. | Collagenase inhibitor (ng/ml) |
|---|---|
| 42 | 200 |
| 43 | 236 |
| 44 | 230 |
| 45 | 191 |
| 46 | 165 |
| 47 | 176 |
| 48 | 210 |
| 49 | 165 |
| 50 | 155 |
| Mean 184 ± 31 | |

TABLE 5 - 2

Sera from patients with hepatocellular carcinoma

| Sample No. | Collagenase inhibitor (ng/ml) |
|---|---|
| 1 | 507 |
| 2 | 342 |
| 3 | 353 |
| 4 | 638 |
| 5 | 648 |
| 6 | 615 |
| 7 | 201 |
| 8 | 648 |
| 9 | 141 |
| 10 | 1109 |
| 11 | 461 |
| 12 | 551 |
| 13 | 2066 |
| 14 | 542 |
| 15 | 648 |
| 16 | 626 |
| 17 | 306 |
| 18 | 206 |
| 19 | 219 |
| 20 | 230 |
| 21 | 839 |
| 22 | 284 |
| 23 | 270 |
| 24 | 342 |
| 25 | 324 |
| 26 | 1062 |
| 27 | 237 |
| 28 | 680 |
| 29 | 461 |
| 30 | 875 |
| 31 | 437 |
| 32 | 1710 |
| 33 | 590 |
| 34 | 708 |
| 35 | 336 |
| 36 | 366 |
| 37 | 278 |
| 38 | 803 |
| 39 | 555 |
| 40 | 177 |
| 41 | 449 |
| 42 | 684 |
| 43 | 248 |
| 44 | 255 |
| 45 | 248 |
| 46 | 183 |
| 47 | 270 |
| 48 | 201 |
| 49 | 201 |
| 50 | 206 |
| 51 | 230 |
| 52 | 626 |
| 53 | 425 |
| 54 | 320 |
| 55 | 731 |
| 56 | 791 |
| 57 | 1062 |
| 58 | 1299 |
| 59 | 698 |

TABLE 5 - 2-continued

Sera from patients with hepatocellular carcinoma

| Sample No. | Collagenase inhibitor (ng/ml) |
|---|---|
| 60 | 437 |
| 61 | 626 |
| 62 | 237 |
| 63 | 672 |
| 64 | 875 |
| 65 | 437 |
| 66 | 507 |
| 67 | 694 |
| 68 | 219 |
| 69 | 284 |
| 70 | 615 |
| 71 | 219 |
| 72 | 447 |
| 73 | 449 |
| 74 | 206 |
| 75 | 248 |
| 76 | 348 |
| 77 | 237 |
| 78 | 791 |
| 79 | 366 |
| 80 | 320 |
| 81 | 248 |
| 82 | 437 |
| 83 | 437 |
| 84 | 1014 |
| 85 | 123 |
| 86 | 348 |
| 87 | 278 |
| 88 | 449 |
| 89 | 336 |
| 90 | 437 |
| 91 | 374 |
| 92 | 314 |
| 93 | 230 |
| 94 | 324 |
| 95 | 519 |
| 96 | 165 |
| 97 | 296 |
| 98 | 219 |
| 99 | 579 |
| 100 | 483 |
| Mean 484 ± 316 | |

TABLE 5 - 3

Sera from patients with metastatic liver carcinoma

| Sample No. | Collagenase inhibitor (ng/ml) |
|---|---|
| 1 | 1952 |
| 2 | 1004 |
| 3 | 558 |
| Mean 1171 ± 712 | |

TABLE 6 - 1

Sera from patients with liver cirrhosis

| Sample No. | Collagenase inhibitor (ng/ml) |
|---|---|
| 1 | 183 |
| 2 | 113 |
| 3 | 116 |
| 4 | 171 |
| 5 | 183 |
| 6 | 206 |
| 7 | 155 |
| 8 | 266 |
| 9 | 237 |
| 10 | 248 |
| 11 | 255 |
| 12 | 320 |
| 13 | 159 |

TABLE 6 - 1-continued

Sera from patients with liver cirrhosis

| Sample No. | Collagenase inhibitor (ng/ml) |
|---|---|
| 14 | 134 |
| 15 | 348 |
| 16 | 366 |
| 17 | 318 |
| 18 | 213 |
| 19 | 230 |
| 20 | 255 |
| 21 | 378 |
| 22 | 38 |
| 23 | 1145 |
| 24 | 183 |
| 25 | 317 |
| 26 | 123 |
| 27 | 278 |
| 28 | 300 |
| 29 | 318 |
| 30 | 101 |
| 31 | 213 |
| 32 | 120 |
| 33 | 155 |
| 34 | 255 |
| 35 | 96 |
| 36 | 141 |
| 37 | 318 |
| 38 | 86 |
| 39 | 51 |
| 40 | 224 |
| 41 | 270 |
| 42 | 119 |
| 43 | 213 |
| 44 | 99 |
| 45 | 224 |
| 46 | 224 |
| Mean 228 ± 163 | |

TABLE 6 - 2

Sera from patients with chronic active hepatitis

| Sample No. | Collagenase inhibitor (ng/ml) |
|---|---|
| 1 | 213 |
| 2 | 389 |
| 3 | 212 |
| 4 | 507 |
| 5 | 206 |
| 6 | 155 |
| 7 | 266 |
| 8 | 242 |
| 9 | 213 |
| 10 | 284 |
| 11 | 278 |
| 12 | 270 |
| 13 | 248 |
| 14 | 183 |
| 15 | 278 |
| 16 | 146 |
| 17 | 114 |
| 18 | 306 |
| 19 | 314 |
| 20 | 324 |
| 21 | 284 |
| 22 | 248 |
| 23 | 188 |
| 24 | 266 |
| 25 | 248 |
| 26 | 288 |
| 27 | 129 |
| 28 | 437 |
| 29 | 206 |
| 30 | 173 |
| 31 | 195 |
| 32 | 336 |
| 33 | 165 |
| 34 | 114 |

TABLE 6 - 2-continued

Sera from patients with chronic active hepatitis

| Sample No. | Collagenase inhibitor (ng/ml) |
|---|---|
| 35 | 108 |
| 36 | 108 |
| 37 | 296 |
| 38 | 137 |
| 39 | 159 |
| 40 | 296 |
| 41 | 137 |
| 42 | 266 |
| 43 | 137 |
| 44 | 278 |
| 45 | 137 |
| Mean 233 ± 88 | |

TABLE 6 - 3

Sera from patients with chronic inactive hepatitis

| Sample No. | Collagenase inhibitor (ng/ml) |
|---|---|
| 1 | 237 |
| 2 | 195 |
| 3 | 165 |
| 4 | 159 |
| 5 | 146 |
| 6 | 206 |
| 7 | 108 |
| 8 | 201 |
| 9 | 201 |
| 10 | 173 |
| 11 | 278 |
| 12 | 402 |
| 13 | 177 |
| 14 | 173 |
| 15 | 177 |
| 16 | 219 |
| 17 | 74 |
| 18 | 81 |
| 19 | 45 |
| 20 | 173 |
| 21 | 119 |
| 22 | 78 |
| 23 | 95 |
| 24 | 147 |
| 25 | 137 |
| 26 | 146 |
| Mean 166 ± 73 | |

TABLE 7

| Plasmas from normal subjects | | Plasmas from patients with hepatocellular carcinoma | |
|---|---|---|---|
| Sample No. | Collagenase inhibitor (ng/ml) | Sample No. | Collagenase inhibitor (ng/ml) |
| 1 | 61 | 1 | 175 |
| 2 | 78 | 2 | 431 |
| 3 | 44 | 3 | 1534 |
| 4 | 70 | 4 | 943 |
| 5 | 75 | 5 | 261 |
| 6 | 84 | 6 | 429 |
| 7 | 70 | 7 | 366 |
| 8 | 54 | 8 | 523 |
| 9 | 49 | | |
| 10 | 74 | | |
| 11 | 73 | | |
| 12 | 64 | | |
| 13 | 72 | | |
| 14 | 62 | | |
| 15 | 67 | | |
| 16 | 54 | | |
| 17 | 74 | | |
| 18 | 51 | | |
| 19 | 57 | | |
| 20 | 53 | | |
| 21 | 60 | | |
| 22 | 60 | | |
| 23 | 64 | | |
| 24 | 56 | | |
| 25 | 62 | | |
| 26 | 74 | | |
| Mean 64 ± 10 | | Mean 583 ± 447 | |

We claim:

1. A screening method to aid in the diagnosis of hepatic carcinoma, comprising:

(a) contacting a sample of serum or plasma suspected of containing collagenase inhibitor with a first insoluble complex composed of a solid substrate having bound thereto a first monoclonal antibody specific for collagenase inhibitor in order to bind said collagenase inhibitor to said insoluble complex;

(b) contacting said insoluble complex with a second monoclonal antibody specific for collagenase inhibitor conjugated to an enzyme so as to form an insoluble ternary complex of said enzyme-conjugated second monoclonal antibody, said collagenase inhibitor, and said solid substrate;

(c) determining the amount of said collagenase inhibitor by incubating said ternary complex with a substrate of said enzyme and determining the amount of said enzyme reaction product formed from a standard curve to provide a measure of the amount of collagenase inhibitor; and (d) comparing the amount of said collagenase inhibitor to that in serum or plasma from normal subjects, wherein an elevation of said amount of collagenase inhibitor is indicative of the presence of hepatic carcinoma.

2. The method of claim 1, wherein said solid substrate is a material selected from the group consisting of polystyrene, polycarbonate, polypropylene, and polyvinyl.

3. The method of claim 1, wherein said solid substrate is in a form selected from the group consisting of a ball, a microplate, a stick, and a test tube.

4. The method of claim 1, wherein said solid substrate is a polystyrene ball.

5. The method of claim 1, wherein said enzyme is horseradish peroxidase.

6. The method of claim 5, wherein said substrate is a substrate for horseradish peroxidase.

7. The method of claim 5, wherein said amount of said collagenase inhibitor is determined by measuring the optical density of the reaction mixture containing said enzyme reaction product formed at 450 nm.

8. The method of claim 1, wherein said standard curve is prepared by measuring the amount of enzyme reaction product formed in reaction mixtures containing varying amounts of human serum collagenase inhibitor.

9. The method of claim 1, wherein said screening further comprises performing liver function tests.

10. The method of claim 11, wherein said liver function tests are selected from the group consisting of the zinc sulfate turbidity test, measurement of glutamic oxaloacetic transaminase, measurement of glutamic-pyruvic transaminase, measurement of alkaline phosphatase, measurement of lactate dehydrogenase, measurement of γ-glutamyl transpeptidase, measurement of prolyl hydroxylase, and measurement of α-fetoprotein.

11. A screening method to aid in the diagnosis of hepatic carcinoma, comprising:
   (a) contacting a sample of serum or plasma suspected of containing collagenase inhibitor with a first insoluble complex comprised of a solid substrate having bound thereto an antibody produced by hybridoma clone FERM BP-3469 in order to bind said collagenase inhibitor to said insoluble complex;
   (b) contacting said insoluble complex with a second monoclonal antibody produced by hybridoma clone FERM BP-3468 conjugated to an enzyme so as to form an insoluble ternary complex of said enzyme-conjugated second monoclonal antibody, said collagenase inhibitor, and said solid substrate;
   (c) determining the amount of said collagenase inhibitor by incubating said ternary complex with a substrate of said enzyme and determining the amount of said enzyme reaction product formed from a standard curve to provide a measure of the amount of collagenase inhibitor; and
   (d) comparing the amount of said collagenase inhibitor to that in serum or plasma from normal subjects, wherein an elevation of said amount of collagenase inhibitor is indicative of the presence of hepatic carcinoma.

12. The method of claim 11, wherein said solid substrate is a material selected from the group consisting of polystyrene, polycarbonate, polypropylene, and polyvinyl.

13. The method of claim 11, wherein said solid substrate is in a form selected from the group consisting of a ball, a microplate, a stick, and a test tube.

14. The method of claim 11, wherein said solid substrate is a polystyrene ball.

15. The method of claim 11, wherein said enzyme is horseradish peroxidase.

16. The method of claim 15, wherein said substrate is a substrate for horseradish peroxidase.

17. The method of claim 15, wherein said amount of said collagenase inhibitor is determined by measuring the optical density of the reaction mixture containing said enzyme reaction product formed at 450 nm.

18. The method of claim 11, wherein said standard curve is prepared by measuring the amount of enzyme reaction product formed in reaction mixtures containing varying amounts of human serum collagenase inhibitor.

19. The method of claim 11, wherein said screening further comprises performing liver function tests.

20. The method of claim 19, wherein said liver function tests are selected from the group consisting of the zinc sulfate turbidity test, measurement of glutamic oxaloacetic transaminase, measurement of glutamic-pyruvic transaminase, measurement of alkaline phosphatase, measurement of lactate dehydrogenase, measurement of γ-glutamyl transpeptidase, measurement of prolyl hydroxylase, and measurement of α-fetoprotein.

* * * * *